United States Patent
Zuk

(10) Patent No.: US 9,468,652 B2
(45) Date of Patent: Oct. 18, 2016

(54) MULTIPURPOSE DENTAL GEL

(71) Applicant: Michael Yar Zuk, Red Deer (CA)

(72) Inventor: Michael Yar Zuk, Red Deer (CA)

( * ) Notice: Subject to any disclaimer, the term of this patent is extended or adjusted under 35 U.S.C. 154(b) by 0 days.

(21) Appl. No.: 14/332,278

(22) Filed: Jul. 15, 2014

(65) Prior Publication Data

US 2016/0015737 A1   Jan. 21, 2016

(51) Int. Cl.
*A61K 31/047* (2006.01)
*A61K 31/155* (2006.01)
*A61K 33/00* (2006.01)
*A61K 47/34* (2006.01)
*A61K 9/00* (2006.01)

(52) U.S. Cl.
CPC ............. *A61K 33/00* (2013.01); *A61K 9/0053* (2013.01); *A61K 31/047* (2013.01); *A61K 31/155* (2013.01); *A61K 47/34* (2013.01)

(58) Field of Classification Search
CPC ........................... A61K 31/047; A61K 31/155
See application file for complete search history.

(56) References Cited

U.S. PATENT DOCUMENTS 5,993,784 A * 11/1999 Hill .......................... A61K 8/25
424/49

* cited by examiner

*Primary Examiner* — Zohreh Fay

(57) ABSTRACT

Some embodiments of the present disclosure include a dental gel formulation for protecting a user's teeth and gums from acid resulting from acid reflux disease or bacterial plaque. The dental gel may include a gel carrier and a treatment ingredient, the treatment ingredient being a member selected from the group consisting of an antibacterial ingredient, an acid neutralizing ingredient, a vitamin, a mineral ingredient, a probiotic, natural extracts and oils, and medication. In some embodiments, the gel carrier may be a poloxamer 407 gel, and the treatment ingredients may include sodium bicarbonate, calcium carbonate, xylitol, and optionally melatonin.

2 Claims, No Drawings

MULTIPURPOSE DENTAL GEL

BACKGROUND

The embodiments herein relate generally to oral health, and more particularly, to a multipurpose dental gel.

The teeth and gums may be damaged by a variety of sources. For example, acid reflux disease, which primarily affects the esophagus, may also damage the teeth. Additionally, bacterial growth on the teeth and gums may occur during use of dental appliances, such as orthodontic retainers, orthodontic aligners, snoring appliances, bruxism appliances, sports protective mouth guards, and the like.

Conventional dental gels include fluoride gels. However, fluoride gels tend to be swallowed, which may present health concerns. Additionally, the use of fluoride gels only reduces tooth decay.

Therefore, what is needed is a physical and chemical barrier for protecting the teeth from acids and the growth of bacteria, while also optionally providing other health benefits.

SUMMARY

Some embodiments of the present disclosure include a dental gel formulation for protecting a user's teeth and gums from acid resulting from acid reflux disease or bacterial plaque. The dental gel may include a gel carrier and a treatment ingredient, the treatment ingredient being a member selected from the group consisting of an antibacterial ingredient, an acid neutralizing ingredient, a vitamin, a mineral ingredient, a probiotic, natural extracts and oils, and medication. In some embodiments, the gel carrier may be a poloxamer 407 gel, and the treatment ingredients may include sodium bicarbonate, calcium carbonate, xylitol, and optionally melatonin.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as a multipurpose dental gel and may comprise the following elements. This list of possible constituent elements is intended to be exemplary only, and it is not intended that this list be used to limit the formulation of the present application to just these elements. Persons having ordinary skill in the art relevant to the present disclosure may understand there to be equivalent elements that may be substituted within the present disclosure without changing the essential function or operation of the device.
  1. Gel Carrier
  2. Treatment Ingredient The various elements of the multipurpose gel formulation for use in dental appliances of the present disclosure may be related in the following exemplary fashion. It is not intended to limit the scope or nature of the relationships between the various elements and the following examples are presented as illustrative examples only.

By way of example, some embodiments of the multipurpose gel formulation of the present disclosure comprise a gel carrier comprising at least treatment ingredient, wherein the treatment ingredient may be a member selected from the group consisting of an antibacterial ingredient, an acid neutralizing ingredient, a vitamin, a mineral ingredient, a probiotic, natural extracts and oils, medication, and a mixture thereof, wherein the gel has a viscosity and thickness configured to substantially retain the gel in the dental appliance while also being easily cleaned out of the dental appliance using, for example, water and a toothbrush. For example, the gel formulation may have a viscosity sufficient to provide a physical barrier on an outer layer of the teeth when the gel formulation is in use.

In embodiments, the gel carrier may be any suitable gel carrier, such as gels which are safe and will not harm the body tissue which will be contacted by the gel carrier. For example, in some embodiments, the gel carrier may be a poloxamer gel or a methyl cellulose gel. In some embodiments, the gel carrier may comprise poloxamer 407 20% gel.

In embodiments, the treatment ingredient may comprise any desired ingredient or combination of ingredients. For example, in some embodiments, the treatment ingredient may be a member selected from the group consisting of an antibacterial ingredient, an acid neutralizing ingredient, a vitamin, a mineral ingredient, a probiotic, natural extracts and oils, medication, and a mixture thereof. The treatment ingredient may be carried by the carrier gel in any desired amount.

In some embodiments, the multipurpose gel formulation may comprise a poloxamer gel containing an amount of sodium bicarbonate, calcium carbonate, xylitol, and optionally melatonin, and the gel formulation may function as an acid reflux formula, wherein the melatonin may help reduce the acid production of the stomach.

In other embodiments, the multipurpose gel formulation may comprise a gel carrier containing xylitol, which may reduce cariogenic bacterial growth, and calcium carbonate for mineralization. In yet further embodiments, the gel formulation may comprise a gel carrier and a probiotic to modify the oral flora, wherein a specific multi-gel formula may be employed for use on alternate evenings/days. For example, bactericidal ingredients, such as chlorhexidine, may be employed in the separate formulation. Some embodiments may further comprise a natural extract formula, such as a natural extract or oil like coconut oil, which may provide certain benefits. In even further embodiments, the gel formulation may comprise a variety of vitamins and minerals to offer specific benefits. Moreover, gel formulations may also comprise medication, wherein the medication may be absorbed directly through the gums.

The percentage of the treatment ingredient in the gel carrier may vary depending on the nature of the treatment of the ingredient and the desired effect of the treatment ingredient.

For example, in some embodiments, the gel formulation of the present disclosure may comprise a mixture of a plurality of Phases, such as Phases A, B, C, and D. In a particular embodiment, Phase A comprises water and xylitol NF; Phase B comprises glycerin, xanthan gum, and sodium bicarbonate; Phase C comprises water, calcium carbonate, melatonin powder, polaxomer 407, and sodium bicarbonate; and Phase D comprises dehydrated alcohol and D-limonene, wherein the amount of Phase A is about 32.8% by weight based on a total weight of the gel formulation, the amount of Phase B is about 6.75% by weight based on a total weight of the gel formulation, the amount of Phase C is about 57.8% by weight based on a total weight of the gel formulation, and the amount of Phase D is about 3.75% by weight based on a total weight of the gel formulation. Particularly, based on 100 g total weight of the gel formulation, Phase A may comprise about 26.8 g of water and 5 g of xylitol NF; Phase B may comprise about 5 g of glycerin, about 0.5 g of xanthan gum, and about 1.25 g of sodium bicarbonate; Phase C may comprise about 40 g of water, 2.5 g of calcium carbonate, 0.05 g of melatonin powder, 15 g of polaxomer 407, and 0.15 g if sodium benzoate; and Phase D may comprise about 3 g of dehydrated alcohol and about 0.85 g of D-limonene. The gel formulation may be made by: (i) adding Phase A to a mixer and mixing Phase A until it is fully dispersed and free of carbopol; (ii) in a separate mixer, adding Phase B to the mixer and mixing Phase B until it is fully dispersed; (iii) adding Phase B to Phase A; (iv) in a separate mixer, mixing Phase D until menthol crystals fully dissolve; (v) adding Phase C to the mixture comprising Phases A and B; and (vi) adding Phase D to the mixture comprising Phases A, B, and C. The resulting gel formulation may be clear in color, may have a viscosity of from about 60,000 to about 96,000, and may have a pH of from about 4.5 to about 5.5. For lighter embodiments with less taste, the amounts of the ingredients other than water and the gel base, such as polaxomer 407, may be reduced. Moreover, in embodiments, the gel formulation may be modified to have a desired pH, which may provide additional desired benefits, such as the gel formulation being acidic enough to remove dental calculus (tartar), but not being so acidic that the dental tissues would be damaged.

To use the gel formulation of the present disclosure, the gel may be applied inside the areas of the dental appliance that may have contact with the teeth and associated structures, such as the gums. For example, the gel formulation may be applied to an orthodontic retainer, a removable aligner, a bruxism appliance, or the like. A user may want to dry the dental appliance before applying the gel formulation to reduce the risk of dilution or reduced viscosity. After applying the gel formulation to the dental appliance, a user would then insert the dental appliance into the mouth as usual. After use, the dental appliance and the mouth may be rinsed with water. In some embodiments, the gel formulation may be packaged in a squeezable container or dispensed from a syringe.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A multipurpose gel formulation for use in dental appliances, the gel formulation comprising Phase A, Phase B, Phase C, and Phase D, wherein:
    Phase A comprises:
        water; and
        xylitol NF;
    Phase B comprises:
        glycerin;
        xanthan gum; and
        sodium bicarbonate;
    Phase C comprises:
        water;
        calcium carbonate;
        melatonin powder;
        polaxomer 407; and
        sodium benzoate; and
    Phase D comprises:
        dehydrated alcohol; and
        D-limonene.

2. The gel formulation of claim 1, wherein, based on the gel formulation having a total weight of about 100 g:
    Phase A comprises about 31.8 g;
    Phase B comprises about 6.75 g;
    Phase C comprises about 57.8 g; and
    Phase D comprises about 3.75 g.

* * * * *